(12) United States Patent
Ehrnsperger et al.

(10) Patent No.: US 7,972,320 B2
(45) Date of Patent: Jul. 5, 2011

(54) ABSORBENT ARTICLE WITH SEGMENTED BELT

(75) Inventors: Bruno Johannes Ehrnsperger, Cincinnati, OH (US); Andrew James Sauer, Cincinnati, OH (US); Gary Dean LaVon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1175 days.

(21) Appl. No.: 11/251,312

(22) Filed: Oct. 14, 2005

(65) Prior Publication Data

US 2007/0088311 A1  Apr. 19, 2007

(51) Int. Cl.
*A61F 13/15* (2006.01)

(52) U.S. Cl. .................... 604/396; 604/385.3; 604/386; 604/392; 604/394

(58) Field of Classification Search ................ 604/396, 604/385.3, 386, 392, 394
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 3,911,173 A | 10/1975 | Sprague, Jr. |
| 4,081,301 A | 3/1978 | Buell |
| 4,253,461 A | 3/1981 | Strickland et al. |
| 4,515,595 A | 5/1985 | Kievit et al. |
| 4,573,986 A | 3/1986 | Minetola et al. |
| 4,610,678 A | 9/1986 | Weisman et al. |
| 4,662,875 A | 5/1987 | Hirotsu et al. |
| 4,669,622 A | 6/1987 | Bennett |
| 4,673,402 A | 6/1987 | Weisman et al. |
| 4,743,246 A | 5/1988 | Lawson |
| 4,785,996 A | 11/1988 | Ziecker et al. |
| 4,834,735 A | 5/1989 | Alemany et al. |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,940,464 A | 7/1990 | Van Gompel et al. |
| 4,946,527 A | 8/1990 | Battrell |
| 4,963,140 A | 10/1990 | Robertson et al. |
| 4,968,312 A | 11/1990 | Khan |
| 4,990,147 A | 2/1991 | Freeland |
| 5,037,416 A | 8/1991 | Allen et al. |

(Continued)

FOREIGN PATENT DOCUMENTS

EP   0 873 739 B1   4/2004

(Continued)

*Primary Examiner* — Jacqueline F Stephens
(74) *Attorney, Agent, or Firm* — John G. Powell; Matthew P. Fitzpatrick

(57) ABSTRACT

A disposable diaper includes a chassis having a front waist region, a back waist region, and a crotch region between the waist regions. The chassis includes laterally opposing closed side edges defining its width, longitudinally opposing front and back waist end edges defining its length, an interior surface and an exterior surface, and including a water-impermneable backsheet. An absorbent assembly is attached to the chassis. A belt structure is disposed in the waist region of the chassis. The belt structure includes a first belt segment, a second belt segment and a third belt segment. The belt segments are disposed longitudinally with respect to each other and the coefficient of friction of at least a portion of one of the first belt segment and third belt segment is greater than the coefficient of friction of at least a portion of the second belt segment.

33 Claims, 11 Drawing Sheets

U.S. PATENT DOCUMENTS

| | | | |
|---|---|---|---|
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,242,436 A | 9/1993 | Weil et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,306,266 A | 4/1994 | Freeland | |
| 5,342,338 A | 8/1994 | Roe | |
| 5,387,207 A | 2/1995 | Dyer et al. | |
| 5,397,316 A | 3/1995 | Lavon et al. | |
| 5,397,318 A | 3/1995 | Dreier | |
| 5,499,978 A | 3/1996 | Buell et al. | |
| 5,507,736 A | 4/1996 | Clear et al. | |
| 5,514,121 A | 5/1996 | Roe et al. | |
| 5,540,671 A | 7/1996 | Dreier | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,616,412 A | 4/1997 | Lin | |
| 5,625,222 A | 4/1997 | Yoneda et al. | |
| 5,653,703 A | 8/1997 | Roe et al. | |
| 5,782,819 A | 7/1998 | Tanzer et al. | |
| 5,804,286 A | 9/1998 | Quantrille et al. | |
| 5,858,013 A | 1/1999 | Kling | |
| 5,865,823 A | 2/1999 | Curro | |
| 5,873,870 A | 2/1999 | Seitz et al. | |
| 5,897,545 A | 4/1999 | Kline et al. | |
| 5,904,673 A | 5/1999 | Roe et al. | |
| 5,931,827 A | 8/1999 | Buell et al. | |
| 5,941,864 A | 8/1999 | Roe | |
| 5,957,908 A | 9/1999 | Kline et al. | |
| 5,977,430 A | 11/1999 | Roe et al. | |
| 5,997,520 A | 12/1999 | Ahr et al. | |
| 6,004,306 A | 12/1999 | Robles et al. | |
| 6,010,491 A | 1/2000 | Roe et al. | |
| 6,013,063 A | 1/2000 | Roe et al. | |
| 6,107,537 A | 8/2000 | Elder et al. | |
| 6,120,487 A | 9/2000 | Ashton | |
| 6,120,489 A | 9/2000 | Johnson et al. | |
| 6,258,076 B1 | 7/2001 | Glaug et al. | |
| 6,364,863 B1 * | 4/2002 | Yamamoto et al. | 604/385.27 |
| 6,417,122 B1 | 7/2002 | Newkirk et al. | |
| 6,432,098 B1 | 8/2002 | Kline et al. | |
| 6,478,784 B1 | 11/2002 | Johnson et al. | |
| 6,482,196 B1 * | 11/2002 | Hisada | 604/385.3 |
| 6,626,879 B1 | 9/2003 | Ashton et al. | |
| 6,641,568 B2 | 11/2003 | Ashton et al. | |
| 6,746,433 B1 | 6/2004 | Shimoe et al. | |
| 6,746,434 B2 | 6/2004 | Johnson et al. | |
| 6,918,900 B2 | 7/2005 | Johnson | |
| 2001/0049516 A1 * | 12/2001 | Shimada et al. | 604/385.11 |
| 2002/0151862 A1 * | 10/2002 | Jitoe et al. | 604/385.29 |
| 2003/0233082 A1 | 12/2003 | Kline et al. | |
| 2004/0092902 A1 | 5/2004 | Hoffman et al. | |
| 2004/0162536 A1 | 8/2004 | Becker et al. | |
| 2005/0165173 A1 | 7/2005 | Autran et al. | |

FOREIGN PATENT DOCUMENTS

| | | |
|---|---|---|
| WO | WO 93/25172 A1 | 12/1993 |
| WO | WO 94/14395 A1 | 7/1994 |
| WO | WO 95/16746 A1 | 6/1995 |
| WO | WO 01/30563 A1 | 5/2001 |

* cited by examiner

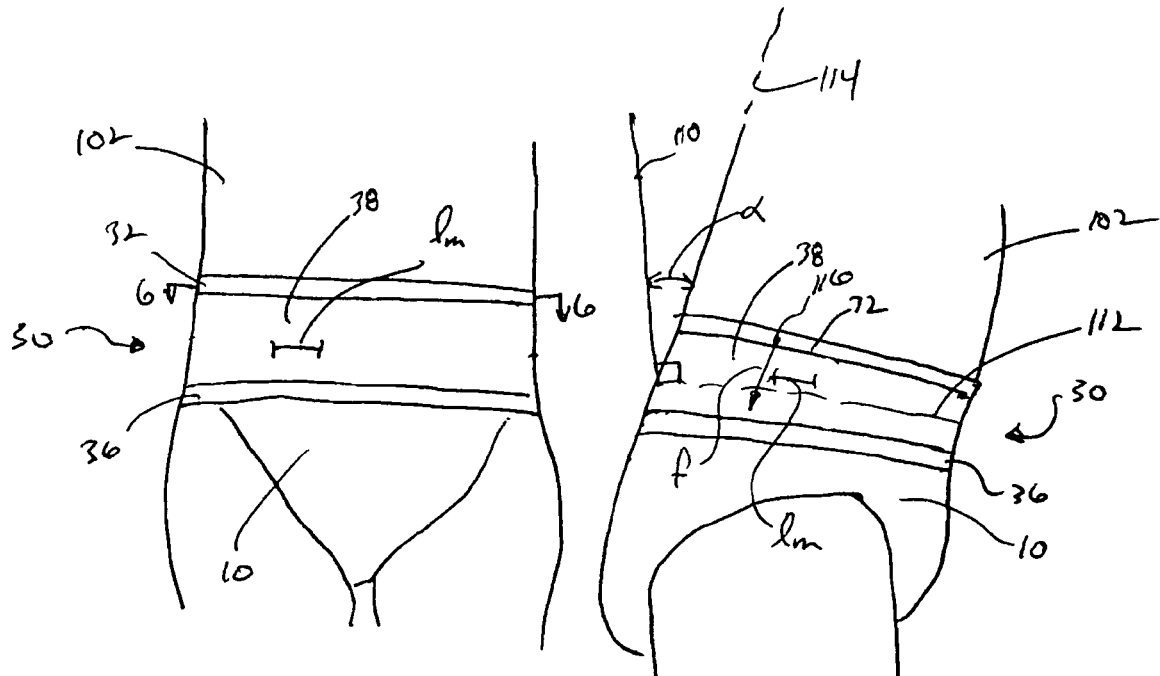
FIG. 4
FIG. 5
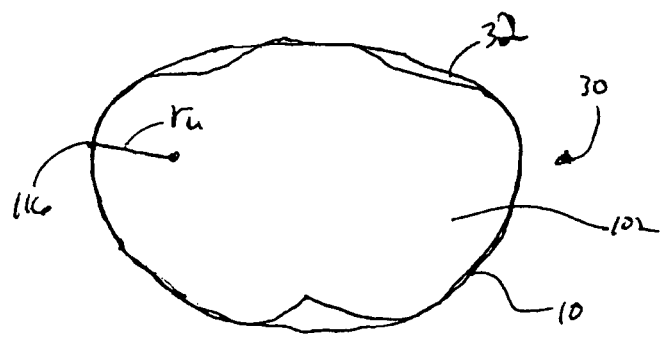
FIG. 6

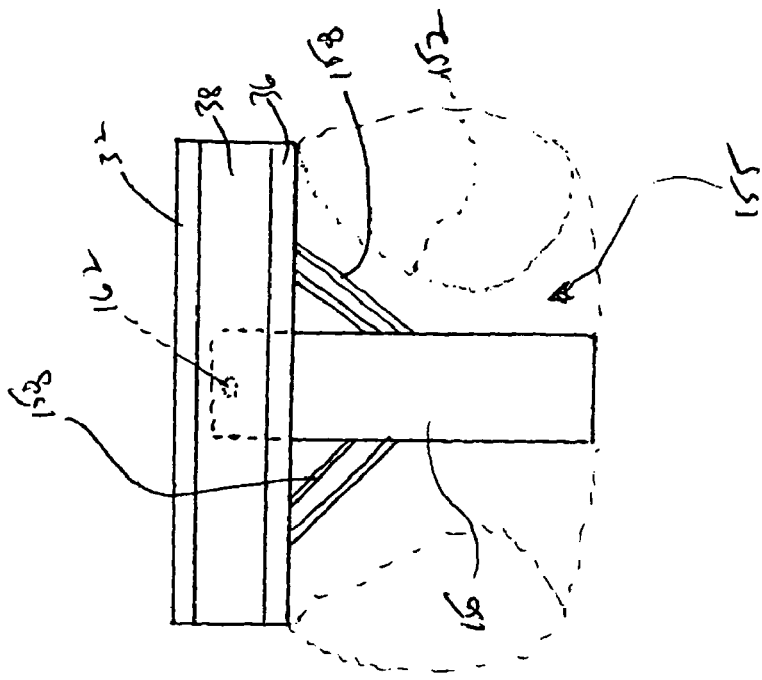
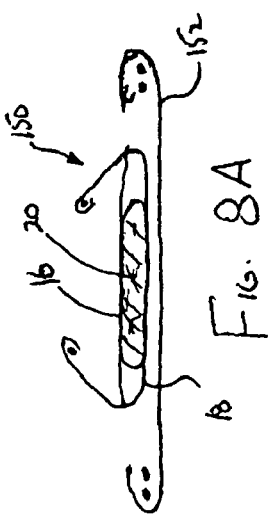
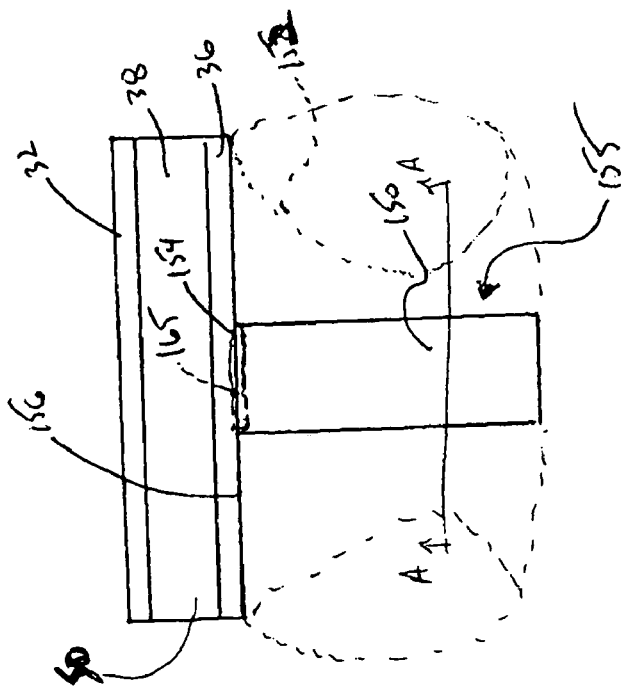
Fig. 9
Fig. 8A
Fig. 8

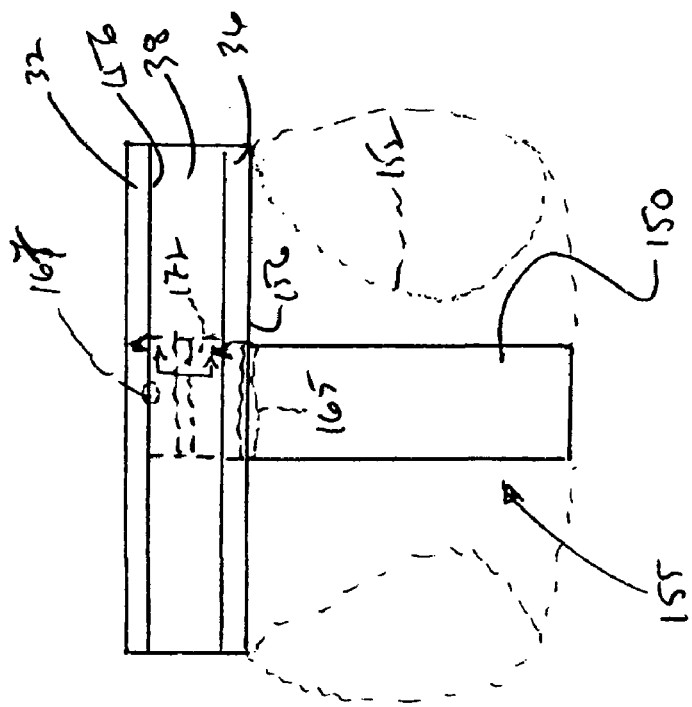
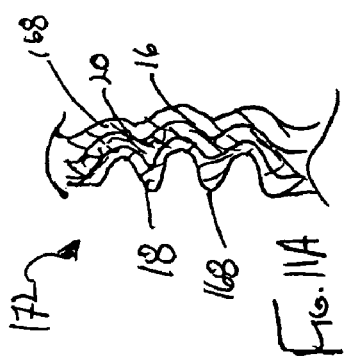
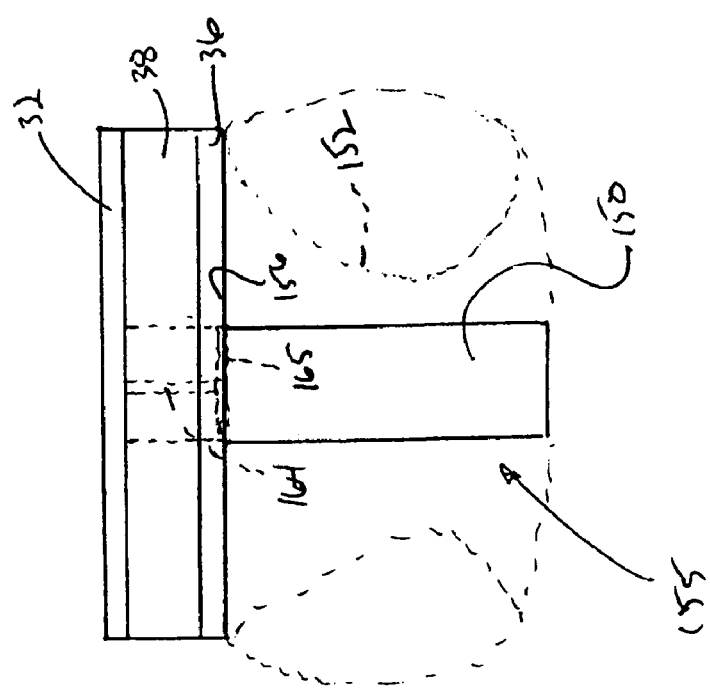

ABSORBENT ARTICLE WITH SEGMENTED BELT

FIELD OF INVENTION

The present application relates to absorbent articles and more particularly to an absorbent article including a segmented belt structure.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments. Disposable absorbent articles having many different basic designs are know to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide or slip down on the body of the wearer during wear. This sagging or gapping and sliding or slipping is caused by the relative motions of the wearer as the wearer breathes, moves, bends and changes positions, by the downward forces generated especially when the absorbent article is loaded with body exudates, and by the deformation of the materials of the absorbent article itself when subjected to such wearer's motions. This sagging or gapping and sliding or slipping of the absorbent article can lead to premature leakage, poor fit and poor coverage of the absorbent article about the wearer in the waist regions and the leg regions of the absorbent article.

In order to more snugly fit absorbent articles about the waist of the wearer, certain commercially available absorbent articles have been provided with elastic waist features. An example of a disposable diaper with an elastic waist feature which has achieved wide acceptance and commercial success is disclosed in U.S. Pat. No. 4,515,595 issued to Kievit and Osterhage on May 7, 1985. Elastic waist features will typically include an elasticized waistband consisting of an elastic member contractibly affixed between the topsheet and the backsheet. The elasticized waistband is designed to expand and contract with the wearer's motions and to maintain the fit of the absorbent article about the waist of the wearer during use (i.e., provide sustained dynamic fit).

However, it has been found that absorbent articles having elastic waist features also have a tendency to sag or gap and slide or slip during use. Further, the elastic waist feature has a tendency to rollover or roll-in at the front of the diaper resulting in a lack of fit about the waist of the wearer.

Thus, it would be advantageous to provide an absorbent article having a waist feature that provides better fit, improved coverage, reduced leakage, and wearer comfort. It would further be advantageous to provide an absorbent article which has reduced sagging, gapping, rollover, or roll-in at the waist of the diaper as well as reduced overall sliding or slipping of the absorbent article or the absorbent core on the wearer during use.

BRIEF SUMMARY OF THE INVENTION

In an aspect, the invention features a disposable diaper including a chassis having a front waist region, a back waist region, and a crotch region between the waist regions. The chassis includes laterally opposing closed side edges defining its width, longitudinally opposing front and back waist end edges defining its length, an interior surface and an exterior surface, and including a backsheet. An absorbent assembly is attached to the chassis. A belt structure is disposed in the waist region of the chassis. The belt structure includes a first segment, a second segment and a third segment. The segments are disposed longitudinally with respect to each other and the coefficient of friction of at least a portion of one of the first segment and third segment is greater than the coefficient of friction of at least a portion of the second segment.

In another aspect, the invention features a method of forming a disposable diaper. The method includes attaching an absorbent assembly to a chassis. The chassis has a front waist region, a back waist region, and a crotch region between the waist regions, laterally opposing closed side edges defining its width, longitudinally opposing front and back waist end edges defining its length, an interior surface and an exterior surface, and includes a backsheet and a topsheet. A belt structure is formed that includes a first belt segment, a second belt segment and a third belt segment. The belt segments are disposed longitudinally with respect to each other and the coefficient of friction of at least a portion of one of the first belt segment and third belt segment is greater than the coefficient of friction of at least a portion of the second belt segment. The belt structure is joined to the chassis.

BRIEF DESCRIPTION OF THE DRAWINGS

FIG. 4 is a front view of an embodiment of an illustrative diaper on a wearer;

FIG. 5 is a side view of the diaper and wearer of FIG. 4;

FIG. 6 is a diagrammatic section view along lines 6-6 of FIG. 4;

FIG. 8 is a front view of an embodiment of an absorbent article;

FIG. 8A is a section view of the absorbent article along line A-A of FIG. 8;

FIG. 9 is a front view of another embodiment of an absorbent article;

FIG. 10 is a front view of another embodiment of an absorbent article;

FIG. 11 is a front view of another embodiment of an absorbent article;

FIG. 11A is a section view of the absorbent article along line A-A of FIG. 11;

DETAILED DESCRIPTION OF THE INVENTION

Figure 1:
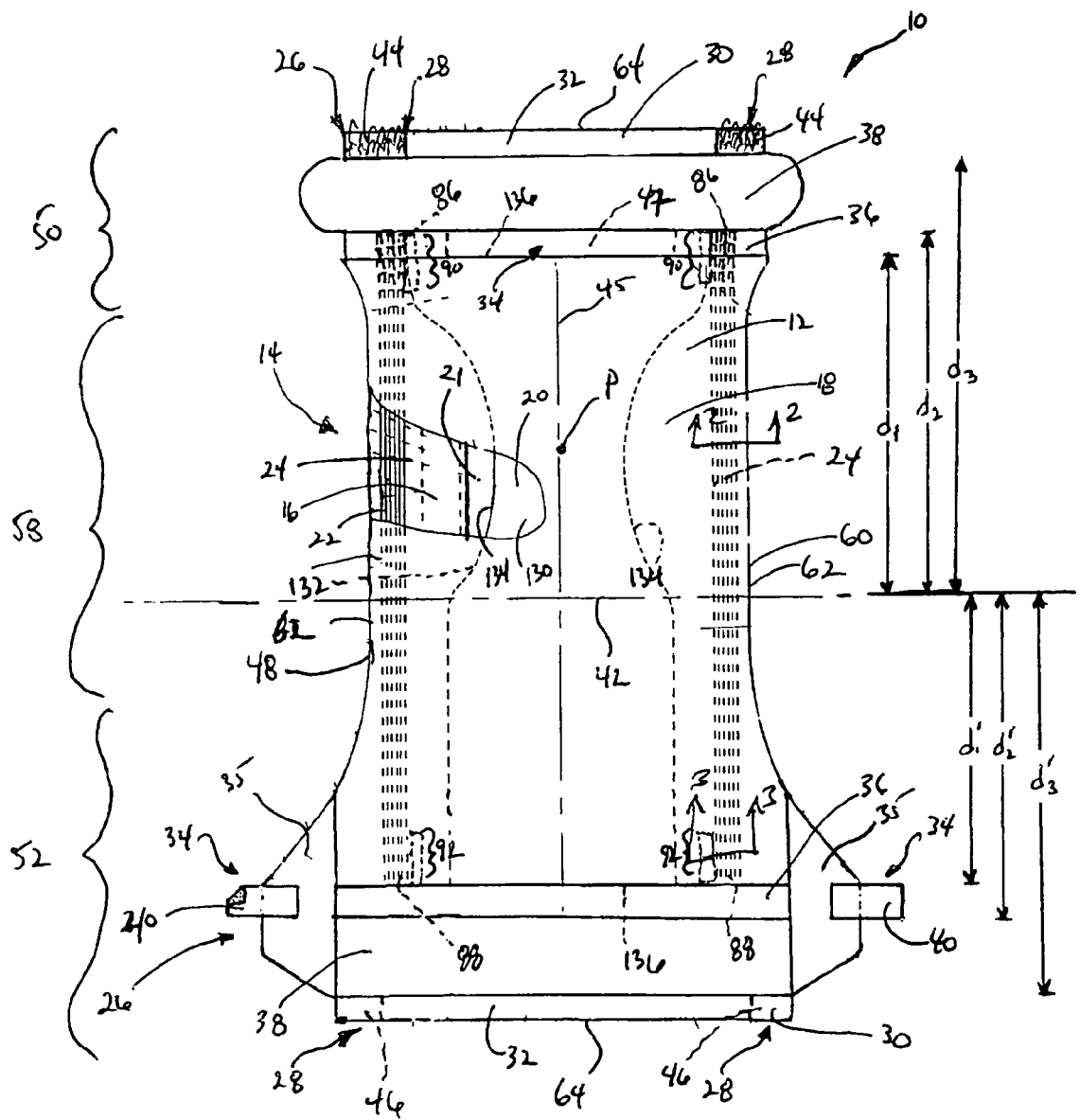
FIG. 1 is a plan view of an embodiment of a diaper.

All documents cited herein are incorporated herein by reference. The citation of any document is not to be construed as an admission that it is prior art with respect to the present invention.

As used herein, the term "absorbent article" refers to devices which absorb and contain body exudates, and, more specifically, refers to devices which are placed against or in proximity to the body of the wearer to absorb and contain the various exudates discharged from the body.

The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

As used herein, the terms "extensible" and "stretchable" refer to materials that are capable of extending in at least one direction to a certain degree without rupture. The terms "elasticity", "elastically extensible" and "elastically stretchable" refer to extensible materials that have the ability to return to approximately their original dimensions after the force that extended the material is removed. As used herein, any material or element described as extensible or as stretchable may also be elastically extensible or elastically stretchable unless otherwise provided.

A "unitary" absorbent article refers to absorbent articles which are formed of separate parts united together to form a coordinated entity so that they do not require separate manipulative parts like a separate holder and liner.

The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Pant examples are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Application No. 2003/0233082, entitled "Highly Flexible And Low Deformation Fastening Device", Published on Dec. 18, 2003; U.S. Pat. No. 5,897,545, issued to Kline et al. on Apr. 27, 1999; U.S. Pat. No. 5,957,908, issued to Kline et al on Sep. 28, 1999.

The terms "liquid-permeable" and "liquid-impermeable" refer to the penetrability of materials in the context of the intended usage of disposable absorbent articles. Specifically, the term "liquid-permeable" refers to a layer or a layered structure having pores, openings, and/or interconnected void spaces that permit a liquid such as water to enter or pass through its thickness in the under typical use conditions (for example without the need to apply a significant or unrepresentative forcing pressure). Conversely, the term "liquid-impermeable" refers to a layer or a layered structure through the thickness of which a liquid such as water cannot pass in the absence of a forcing pressure (for example, under typical in use conditions). A layer or a layered structure that is liquid-impermeable according to this definition may be permeable to liquid vapor, i.e., may be "vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association). As used herein, the term "barrier cuff" refers to an elasticized flap which stands substantially upright, more preferably inwardly towards the longitudinal centerline, within the crotch region. Typically, said barrier cuff envelopes or contains at least one elastic that is connected primarily at its opposing ends to the diaper (e.g., drawstring technique for better fit).

As used herein, the term "gasketing cuff" refers to an elasticized flap which does not stand substantially upright, or which more preferably is disposed outwardly towards the longitudinal side edges of the diaper, within the crotch region. Typically, said gasketing cuff envelopes or contains at least one elastic that is connected substantially throughout its length to the diaper (e.g., multiple bonds along length of elastic to create gathers).

As used herein, the term "belt structure" refers to a structure that is used to support a load on the body and includes one or more components that are worn about the waist. It should be noted that the term belt structure encompasses structures where not all of the belt structure components extend entirely about the waist. For example, a multi-segment belt structure may have a segment that extends about only a portion or portions of the waist (e.g., at the wearer's front and back and not about the sides). A belt segment may also be discontinuous. Additionally, the belt structure may have only one or some components that are primary load-supporting members, while another component or components support little to no load, for example, other than its own weight.

An exemplary embodiment of an absorbent article is the unitary disposable absorbent article, diaper 10, shown in FIG. 1. As used herein, the term "diaper" refers to an absorbent article generally worn by infants and incontinent persons that is worn about the torso of the wearer. It should be understood, however, that the present invention is also applicable to other absorbent articles such as incontinent briefs, incontinent undergarments and the like.

FIG. 1 is a plan view of the diaper 10 of the present invention in its flat-out, uncontracted state (i.e., with elastic induced contraction pulled out except in the side panels wherein the elastic is left in its relaxed condition) with portions of the structure being cut-away to more clearly show the construction of the diaper 10 and with the portion of the diaper 10 which faces away from the wearer, the outer surface 12, facing the viewer. As shown in FIG. 1, the diaper 10 includes a containment assembly 14 including a liquid pervious topsheet 16, a liquid impervious backsheet 18 joined with the topsheet 16, an absorbent core 20 including acquisition system 21 positioned between the topsheet 16 and the backsheet 18, elasticized gasketing cuffs 22, elasticized barrier leg cuffs 24, a segmented belt structure 30 and a closure system comprising a dual tension fastening system generally designated as 26. The dual tension fastening system 26 includes a first fastening system 28 associated with an upper belt segment 32 and a second fastening system 34 associated with a lower belt segment 36 with an intermediate belt segment 38 located at a longitudinal position between the upper and lower belt segments 32, 36. As used herein, the term "longitudinal" refers to a direction substantially parallel to a longitudinal centerline 45 of the diaper 10 and includes directions within ±45° of the longitudinal direction, while the term "lateral" refers to a direction substantially parallel to a lateral centerline 42 of the diaper 10 which is substantially transverse to the longitudinal centerline 45. The second fastening system 34 includes a pair of securement members 40 and a landing member 47. The first fastening system 28 is shown in the embodiment of FIG. 1 to include a pair of first attachment components 44 and a pair of second attachment components 46.

The diaper 10 is shown in FIG. 1 to have the outer surface 12 (facing the viewer in FIG. 1), an inner surface 48 opposed to the outer surface 12, a front waist region 50, a back waist region 52 opposed to the front waist region 50, a crotch region 58 located between the first and back waist regions and a periphery 60 which is defined by the outer edges of the diaper 20 in which the longitudinal edges are designated 62 and the end edges are designated 64. A crotch point P is centrally located within the crotch region 58 of the core 20. The inner surface 48 (or body-facing surface) of the diaper 10 includes that portion of the diaper 10 which is positioned adjacent to the wearer's body during use (i.e., the inner surface 10 generally is formed by at least a portion of the topsheet 16 and other components joined to the topsheet 16). The outer surface 12 (or garment-facing surface) includes that portion of the diaper 10 which is positioned away from the wearer's body (i.e., the outer surface 12 generally is formed by at least a portion of the backsheet 18 and other components joined to the backsheet 18). The front waist region 50 and the back waist region 52 extend, respectively, from the end edges 64 of the periphery 60 to the crotch region 58 of the diaper 10.

FIG. 1 shows a preferred embodiment of the diaper 10 in which the topsheet 16 and the backsheet 18 have length and width dimensions generally larger than those of the absorbent core 20. The topsheet 16, the barrier cuff 24 fabric and the backsheet 18 extend beyond the edges of the absorbent core 20 to thereby form at least a portion of the periphery 60 of the diaper 10. While the topsheet 16, the backsheet 18, and the absorbent core 20 may be assembled in a variety of well-known configurations, exemplary diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Buell on Sep. 9, 1992; and U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999.

The topsheet 16 is compliant, soft feeling, and non-irritating to the wearer's skin. Further, the topsheet 16 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. In some embodiments, the topsheet 16 is made of a hydrophobic material to isolate the wearer's skin from liquids contained in the absorbent core 20.

In an embodiment, at least a portion of the topsheet 16 is subjected to mechanical stretching in order to provide a "zero strain" stretch laminate that forms the elasticized side panels 35. Thus, the topsheet 16 may be elongatable, may be drawable, but not necessarily elastomeric, so that the topsheet 16 may, upon mechanical stretching, be at least to a degree permanently elongated such that it will not fully return to its original configuration. In certain embodiments, the topsheet 16 can be subjected to mechanical stretching without undue rupturing or tearing of the topsheet. Thus, the topsheet 16 may have a low cross-machine direction (lateral direction) yield strength. In some embodiments, at least a portion of the topsheet 16 may contain elastomeric fibers or bico-fibers, with one component being an elastomeric polymer (e.g., polyurethane, polyethylene, VISTAMAXX fibers available from Exxon Mobil Corporation, etc.)

There are a number of manufacturing techniques which may be used to manufacture the topsheet 16. For example, the topsheet 16 may be a nonwoven web of fibers. When the topsheet 16 comprises a nonwoven web, the web may be spunbonded, carded, wet-laid, meltblown, hydroentangled, combinations of the above, or the like. In some embodiments, topsheet 16 is carded and thermally bonded by means well known to those skilled in the fabrics art. In some instances, topsheet 16 includes staple length polypropylene fibers having a denier of about 2.2. As used herein, the term "staple length fibers" refers to those fibers having a length of at least about 15.9 m (0.625 inches). In, certain implementations, the topsheet 16 has a basis weight from about 18 to about 25 grams per square meter. A suitable topsheet 16 is manufactured by Veratec, Inc., a Division of International Paper Company, of Walpole, Mass. under the designation P-8. Other examples of topsheets 16 having desirable mechanical characteristics after activation of the segmented belt structure 30 are, for example, disclosed in U.S. Pat. No. 5,804,286 issued to Quantrille et al. on Sep. 8, 1998 entitled "Extensible Composite Nonwoven Fabrics"; U.S. Pat. No. 5,616,412 issued to Lin on Apr. 1, 1997 entitled "Process for Preparing Low Denier Filaments with High Elongation and Those Filaments"; U.S. Pat. No. 6,417,122 issued to Newkirk et al. on Jul. 9, 2002 entitled "Multicomponent Fibers and Fabrics Made Using the Same"; U.S. Pat. application no. 2005/0165173 filed Jan. 25, 2005; WO 01/30563 entitled "Elastic Laminate Employing Nonwoven Formed By Bi-Component Fibers of Ethylene-Propylene Random Copolymer."

The topsheet 16 may be fully or partially elasticized or may be foreshortened so as to provide a void space between the topsheet 16 and the core 20. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets."

The backsheet 18 is generally that portion of the diaper 10 positioned adjacent the garment-facing surface of the absorbent core 20. Backsheet 18 may prevent the exudates absorbed and contained therein from soiling articles that may contact the diaper 10, such as bed sheets and undergarments. In some embodiments, the backsheet 18 is substantially impermeable to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing exudates from passing through the backsheet 18. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex; under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and US. Pat. No. 5,865,823 issued to Curro on Feb. 2, 1999. Other breathable backsheets including nonwoven webs and apertured formed films are described in U.S. Pat No. 5,571,096 issued to Dobrin et al. on Nov. 5, 1996. An exemplary, suitable backsheet 18 is disclosed in U.S. Pat. No. 6,107,537 entitled "Disposable absorbent articles providing a skin condition benefit" issued to Elder et al on Aug. 22, 2000. Other suitable materials and/or manufacturing techniques may be used to provide a suitable backsheet 18 including, but not limited to, surface treatments, particular film selections and processing, particular filament selections and processing, etc.

Backsheet 18 may also consist of more than one layer wherein a backsheet outer layer (often referred to as the backsheet) may be made of a soft, non-woven material and a backsheet inner layer may be made of a substantially impermeable film. Adhesive or any other suitable material or method may be used to join layers and together. While a variety of backsheet configurations are contemplated herein, it would be obvious to those skilled in the art that various other changes and modifications can be made.

Figure 2:
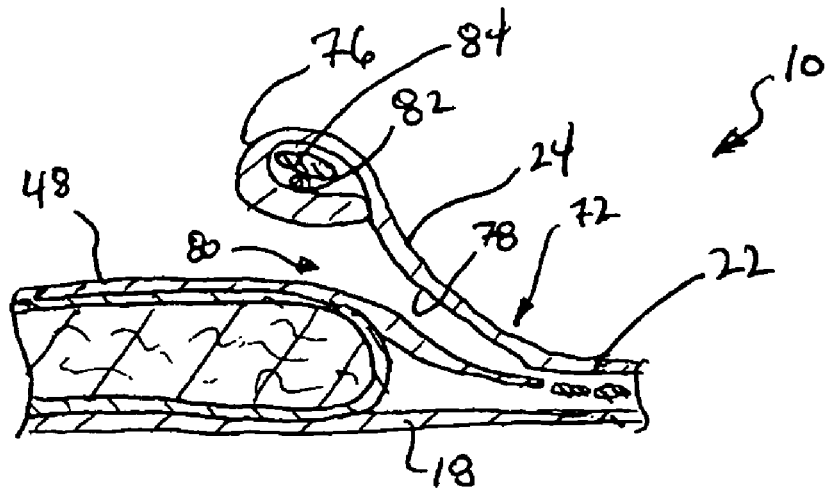
FIG. 2 is a section view along line 2-2 of FIG. 1.

As shown in FIG. 2, the barrier leg cuff 24, and more particularly distal edge 76, is disposed inboard of and preferably adjacent to gasketing cuff 22. The term "inboard" is defined as the direction toward the centerline (45 or 42, respectively) of the diaper 10 that is parallel to the respective edge of the diaper along which the particular gasketing cuff 22 is disposed. The barrier leg cuff 24 is disposed inboard of the gasketing cuff 22 so that exudates, especially loose fecal material which is not easily absorbed and tends to float along a topsheet top surface 48, will contact the barrier leg cuff 24 before it can contact the gasketing cuff 22. The barrier leg cuff 24 is disposed adjacent the gasketing cuff 22 to provide a more effective dual restraint against the flow of body exudates.

Proximal edge 72, which in the illustrated embodiment is generally defined between bonds 75 (FIG. 3), and the distal edge 76 are in spaced relation to each other and define the width of the barrier leg cuff 24. In some embodiments, the proximal edge 72 may be defined by a continuous bond. The proximal and distal edges 72, 76 may be in a parallel, non-parallel, rectilinear, or curvilinear relationship. In addition, the barrier leg cuff 24 may have a variety of different cross-sectional areas including circular, square, rectangular, or any other shape such as shown in FIG. 2. The proximal edge 72 may be spaced from the distal edge 76 in a parallel and rectilinear relationship to provide a barrier leg cuff 24 having uniform width. Each barrier cuff 24 may have a width of at least 5 mm and may be approximately 10-50 mm in width. The barrier cuff 24 may be formed from a folded structure in which portions of the cuff material may be folded back upon itself at one or more locations. In such constructions the distal and proximal edges usually are the most inboard and outboard locations of the cuff material with regard to any folding back of such cuff material.

Each barrier cuff 24 may be joined to the topsheet 16 which includes any means for affixing the barrier cuff 24 to the diaper 10, and includes embodiments wherein the barrier leg cuff 24 is a separate element having a proximal edge 72 directly or indirectly attached to the topsheet 16 or embodiments wherein the barrier leg cuff 24 is made from the same element or material as the topsheet 16 so that the proximal edge 72 is a continuous and undivided element of the topsheet 16. In some embodiments such as the one shown, the barrier leg cuff 24 may be joined to the backsheet 18 or, in some implementations, the barrier leg cuff may be joined to the absorbent core 20, or any combination of these or other elements of the diaper 10. The barrier leg cuff 24 may be formed by a single strip of material which is bonded to the topsheet 16 by bond 75, the distal edge 76 being formed by folding an end of the material back upon itself. The barrier leg cuff 24 can also be formed out of the same material as the topsheet 16 or the backsheet 18 or by the combination of the topsheet and backsheet materials. Additionally, the barrier leg cuff 24 may be formed out of a portion of the core assembly.

Figure 3:
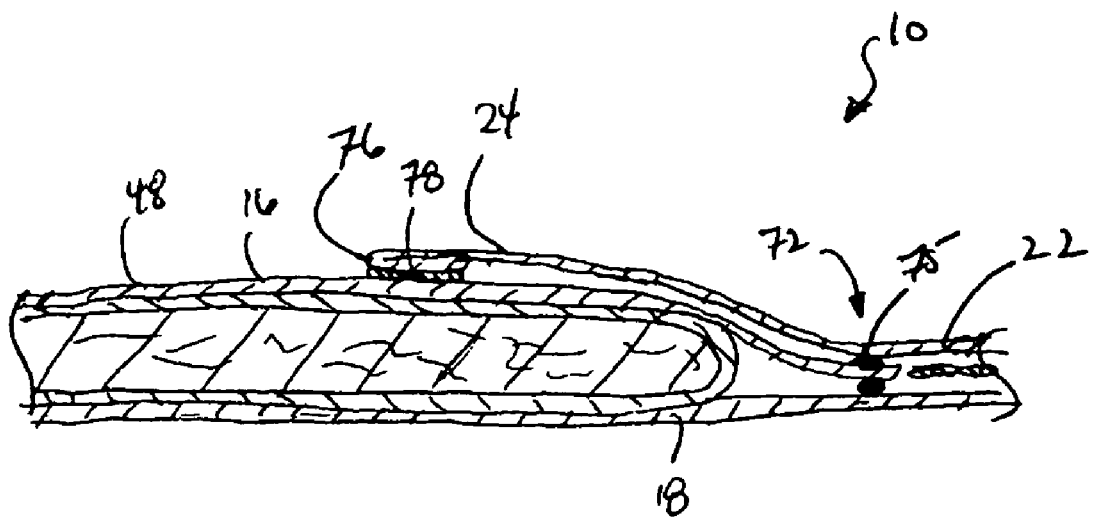
FIG. 3 is a section view along line 3-3 of FIG. 1.

The distal edge 76 may be disposed inboard of the proximal edge 72 to present a more effective barrier against the flow of exudates. The distal edges 76 are maintained inboard of the proximal edges 72 by a bond 78 (such as adhesive, thermal bonds, pressure bonds, ultrasonic bonds, etc.; FIG. 3) so as to obviate their inversion. The distal edge 76 may be unsecured to any other element in at least the crotch region 58 of the diaper 10 so that it may be spaced away from the topsheet 16. The distal edge 76 may be spaced from the topsheet 16 so that the barrier leg cuff 24 may form a channel 80 to enhance containment of the article which includes embodiments wherein the distal edges 76 may assume one or more positions relative to the topsheet 16 including at some times assuming a position adjacent the topsheet. The distance between the distal edge 76 to the topsheet 16 is measured along a line drawn from the distal edge 76 to the closest part of the topsheet when the distal edge 76 is positioned so as to be spaced away from the topsheet as far as possible (i.e., in the elastically contracted position). The distal edge 76 may be spaced away from the topsheet 16 by a height of at least 2 mm or more may be spaced from about 5 mm to about 50 mm.

The channel 80 is formed at least along the proximal and distal edges 72, 76 and inboard surface 78 of the barrier leg cuff 24. The channel 80 forms a barrier to the flow of exudates as they tend to move or float across the topsheet 16. Thus, the channel 80 holds and contains exudates until the diaper 10 can be removed. The barrier leg cuffs 24 may be provided with absorbent material and/or may be rendered liquid impermeable as disclosed in U.S. Pat. No. 4,743,246 which issued to Lawson on May 10, 1988.

A spacer 82 for spacing the distal edge 76 away from the topsheet 16 is any member which gathers, contracts, stiffens, shortens, or otherwise acts on the barrier leg cuff 24 so as to cause a channel 80 to be formed along the barrier leg cuff to provide a constraint against the leakage of exudates. As shown in FIG. 2, the spacer 82 may include a spacing elastic member 84 secured adjacent the distal edge 76 inside the barrier leg cuff 24. The spacing elastic member 84 is preferably secured to the barrier leg cuff 24 in an elastically contractible condition so that in a normally unrestrained configuration, the spacing elastic member 84 effectively contracts or gathers the barrier leg cuff. The spacing elastic member 84 can be secured to the barrier leg cuff 24 in an elastically contractible condition in at least two ways as is discussed in the above-referenced U.S. Pat. No. 3,860,003 issued to K. B. Buell. In addition, the length of the spacing elastic member 84 in general is dictated by the diaper design. In the embodiment illustrated in FIG. 1, the spacing elastic member 84 extends essentially the entire length of the barrier leg cuff 24 in the crotch region 58, although other lengths are cognizable. Additional details and alternatives for the spacer are discussed in the above-referenced U.S. Pat. No. 4,743,246 to Lawson.

Bonds 78 for securing end portions 86 and 88 of the barrier leg cuff 24 closed are shown in FIG. 3. The bonds 78 provide a more comfortable fit for the wearer and obviate inversion of the distal edges 76 of the barrier cuff 24 during application and use. Inversion is generally defined as the inboard disposed distal edge 76 turning outwardly when the diaper 10 is applied to the wearer. In the embodiment illustrated at FIG. 1, such bonds are disposed in the front waist region 50 and the back waist region 52 of the diaper in a front closure zone 90 and a back closure zone 92, respectively. Except as noted below, the remaining portions of the barrier leg cuff 24 are unbonded so that the distal edges 76 are generally left freely openable.

Referring still to FIG. 1, belt structure 30 is formed by the upper, intermediate and lower belt segments 32, 38 and 36, respectively, that are disposed longitudinally with respect to each other. Upper belt segment 32 and lower belt segment 36 each include at least a portion having a higher coefficient of friction than at least a portion of the intermediate belt segment 38. As will be described in greater detail below, the intermediate belt segment 38 serves, at least to an extent, to decouple the lower belt segment 36 and the core 20 from the upper belt segment 32 while the lower belt segment 36 anchors the absorbent assembly to the user's body during use. Such a segmented belt structure 30 can reduce diaper sag, improve diaper fit and converage.

Without wishing to be bound by theory, it is believed that the segmented belt structure 30 is particularly effective if most of the loads (e.g., the loaded core, the elastics from the barrier and gasketing cuff etc.) are coupled or anchored at the lower belt 36. FIGS. 4-7 show a preferred belt structure 30 position on a wearer 102 where the lower belt segment 36 is located at a minimum circumference hoop and in a low motion zone of the body of the wearer. Due to this location of the lower belt segment 36, eventhough the lower belt segment may have little or no lateral extensibility, the diaper 10 may still be comfortable for the wearer 102. In some embodiments, a belt structure 30 with little or no lateral extensibility that is placed at the minimum circumference hoop of the body will inhibit or even prevent sag under substantial loads such as 100 g or more, such as between about 100 g and about 225 g. It has been found, however, that embodiments having a lower belt segment 36 with some or even substantial lateral extensibility may not sag and may provide improved fit and coverage where the lower belt segment 36 has a tension of about 1 N or more, particularly in instances where the lower belt segment has a high coefficient of friction.

Upper belt segment 32 serves to cover skin of the wearer 102, particularly at the stomach. If the upper belt segment 32 is sufficiently decoupled from the lower belt segment 36, the upper belt segment 32 essentially need only to support its own weight to prevent its own sagging, which can be achieved with an upper belt segment 32 that maintains at least about 1 N of lateral tension. In order to be comfortable and to conform to the wearer's movements, for example, due to breathing a relatively flat stress-strain curve, low hysteresis and low stress relaxation are desirable for the upper belt structure 32. In some embodiments, the upper belt segment 32 may be capable of stretching up to about 50 percent without increasing tension beyond a desirable limit. In order for the upper belt segment 32 to move with skin of the wearer 102 it is preferable that the upper belt segment 32 has a high coefficient of friction, is non-extensible in the longitudinal direction and has a width of between about 1 cm and about 4 cm, such as a width of about 2 cm. The upper belt segment 32 may also have some stiffness and/or bending rigidity to inhibit roll over and waist flip over.

Intermediate belt segment 38 serves to decouple the upper and lower belt segments 32 and 36 while covering the wearer's skin in a comfortable and fit-conforming manner preferably without forming wrinkles. In some embodiments, the intermediate belt segment 38 decouples the upper and lower belt segments 32 and 36 as the longitudinal distance between the upper and lower belt segments changes by as much as 50 percent or more due to the wearer's movements (e.g., bending forward or backward, lifting arms over the head, etc.). Sufficient decoupling may be provided by the intermediate belt segment 38 where the coefficient of friction of the intermediate belt segment is low, which can allow the intermediate belt segment to slide over the skin and uniformly stretch in the longitudinal direction. Without wishing to be bound by theory, a simplified criterion for indicating reduced upper belt segment 32 waist sag is given by:

$$\frac{F_m}{l_m} \leq (CoF_u \cdot \cos\alpha + \sin\alpha) \cdot \frac{T_u}{r_u}$$

where, $F_m$ is the longitudinal tension in any part of the intermediate belt segment 38;

$l_m$ is the lateral width of the intermediate belt segment 38;

$CoF_u$ is the coefficient of friction of the upper belt segment 32;

$T_u$ is the lateral tension of the upper belt segment 32;

$r_u$ is the radius of curvature of the upper belt segment 32; and

α is the cone angle.

FIGS. 4-6 illustrate variables of the no sag criterion. More specifically, FIG. 4 is a front view of the diaper 10 on the wearer 102 having an upper tension band provided by the upper belt segment 32 that is decoupled from the lower belt segment 36 by the intermediate belt segment 38. Width $l_m$ of the intermediate belt segment 38 is shown by both FIGS. 4 and 5. The cone angle ☐ is illustrated by FIG. 5 and is measured as the angle of the diaper 10 with respect to a reference line 110 extending normal to the plane of a centerline 112 of the tension band formed by the upper belt segment 32 and a line 114 tangential to the wearer's surface. The radius of curvature $r_u$ is the curvature of the tension band formed by the upper belt segment 32 at the anchoring point 116, as illustrated in FIG. 6.

The above no sag criterion indicates that a lower $F_m$ reduces the tendency of sagging of the upper belt segment 32. The no sag criterion also suggests that it is desirable to provide a high coefficient of friction of the upper belt segment at the front and the back of the wearer.

With renewed reference to FIG. 1, segmented belt structure 30 is formed in light of the above no sag criterion. Upper belt segment 32 (or at least a portion of the upper belt segment) has a relatively high coefficient of friction (static and/or kinetic, e.g., of about 0.8 or greater, such as about 1.0 or greater, about 1.2 or greater) and is elastically stretchable in the lateral direction. The upper belt segment 32 may have a substantially flat stress-strain curve (low hysteresis and low force relaxation). It should be noted, however, that it may be desirable, e.g., from a wearer or consumer standpoint to provide an upper belt segment 32 having lateral stretchability with a non-flat stress-strain curve, for example, so that the higher forces are perceived the more the upper belt segment is stretched. In some embodiments, the upper belt segment 32 may or may not be elastically stretchable in the longitudinal direction. Upper belt segment 32 can be of any suitable width such as, for example, between about 1 cm and about 4 cm, such as about 2 cm in width. When the wearer is standing upright, upper edge 64 of upper belt segment 32 is located in a higher motion region of the body and may extend horizontally about the body and is, in some embodiments, located slightly above (e.g., about 0-2 cm) or below (e.g., about 0-2 cm) the navel of the body.

Lower belt segment 36 (or at least a portion of the lower belt segment) also has a relatively high coefficient of friction (static and/or kinetic, e.g., of about 0.8 or greater, such as about 1.0 or greater, about 1.2 or greater) and is elastically stretchable in the lateral direction. The lower belt segment 36 may have a substantially flat stress-strain curve (low hysteresis and low force relaxation). Like upper belt segment 32, it may be desirable, e.g., from a wearer or consumer standpoint to provide a lower belt segment 36 having lateral stretchability with a non-flat stress-strain curve, for example, so that the higher forces are perceived the more the upper belt segment is stretched. In some embodiments, the lower belt segment 36 may or may not be elastically stretchable in the longitudinal direction. Lower belt segment 36 can be of any suitable width such as, for example, between about 1 cm and about 4 cm, such as about 2 cm in width. When the wearer is standing upright, lower belt segment 36 is located in a lower motion region of the body and may extend horizontally about a hoop of minimum distance around the belly above the hips at the lower abdomen and above the buttocks.

Intermediate belt segment 38 serves to decouple the upper and lower belt segments 32 and 36. Intermediate belt segment 38 (or at least a portion of the intermediate belt segment) has a relatively low coefficient of friction (static and/or kinetic, e.g., of about 0.9 or less, such as about 0.7 or less, such as about 0.5 or less) and is elastically stretchable in both the lateral and longitudinal directions. Preferably, the intermediate belt segment 38 is elastically stretchable with low return force (such as about 0.075 N/mm or less at about 75 percent extension, such as about 0.05 N/mm or less at about 75 percent extension) in the lateral and/or longitudinal direction. Intermediate belt segment 38 may be of any suitable (unstretched) width such as, for example, between about 5 and about 7 cm in width. Desirably, the intermediate belt segment 38 is under little to no tension in the longitudinal direction upon initial positioning of the intermediate belt segment about the baby. By decoupling the upper and lower belt segments 32, 36, influence on the upper belt segment 32 due to body movement during use can be reduced.

Each belt segment 32, 36 and 38 of each waist region 50, 52 is spaced longitudinally from the lateral centerline 42. In region 50, upper belt segment 32 is spaced a distance $d_3$, intermediate belt segment 38 is spaced a distance $d_2$ and lower belt segment 36 is spaced a distance $d_1$ from the centerline 42. In region 52, upper belt segment 32 is spaced a distance $d_3'$, intermediate belt segment is spaced a distance $d_2'$ and lower belt segment 36 is spaced a distance $d_1'$ from the centerline 42. In some embodiments, the distances from the centerline 42 to one or more of the belt segments 32, 36, 38 of one waist region are substantially the same as the distances from the centerline 42 to the corresponding belt segments 32, 36, 38 of the opposing waist region. In some embodiments, the distances from the centerline 42 to one or more of the belt segments 32, 36, 38 of one waist region are different from the distances from the centerline 40 to the corresponding belt segments 32, 36, 38 of the opposing waist region. In some embodiments, the distance between the crotch point P and upper belt segment in one of the waist regions is greater than the distance between the crotch point and the upper belt segment in the opposing waist region. While $d_1$, $d_1'$, $d_2$, $d_2'$, $d_3$ and $d_3'$ are shown as being substantially constant along the length of the respective belt segments 32, 36 and 38, in some embodiments, $d_1$, $d_1'$, $d_2$, $d_2'$, $d_3$ and $d_3'$ change along the length of the belt segments in one or both of the waist regions 50, 52. In other words, one or more of the belt segments 32, 36, 38 of one or both waist regions 50, 52 may have a portion closer to centerline 42 than a different portion of the same belt segment. In some embodiments, the lower belt segment 32 may be sized and arranged to follow the minimum circumference path of the hips of the wearer during use.

As indicated above, the upper and/or lower belt segments 32 and 36 each include at least a portion having a higher coefficient of friction than at least a portion of the intermediate belt segment 38. In some embodiments, at least a portion of the upper or lower belt segment 32, 36 has a coefficient of friction that is greater than a portion of the other of the upper or lower belt segment 32, 36. In certain embodiments, the coefficient of friction of at least a portion of the lower belt segment 36 is substantially equal to the coefficient of friction of the upper belt segment 32.

The upper belt segment 32, intermediate belt segment 36 and lower belt segment 38 may be formed of any suitable material and by any suitable process. As one example, the upper, intermediate and lower belt segments 32, 38 and 36 may be formed using the topsheet 16 and/or backsheet 18 by processing the topsheet and/or backsheet to achieve the above described properties. In some embodiments, the topsheet 16 (e.g., at the body-facing side) may be coated with a material (e.g., as dots of material, lines of material, combinations of dots and lines of material, intersecting lines of material, zigzag lines of material, randomly applied material segments, etc.) such as an elastomer such as silicone, rubber (e.g., synthetic rubber) or polystyrene block copolymer to provide the upper belt segment 32 and the lower belt segment 36. In certain embodiments, only discrete regions or portions of the upper belt segment 32 and/or the lower belt segment 36 includes higher coefficient of friction material, for example, with regions laterally adjacent the higher friction material regions having a lower coefficient of friction. Non-woven materials may include, for example, elastomeric strands that increase the coefficient of friction of the material at the upper and lower belt segments 32, 36. In some embodiments, only the body-facing side of the upper and/or lower belt segment 32, 36 may include higher friction material.

The upper, intermediate and/or lower belt segments 32, 38, 36 may be formed at least in part by activating the topsheet 16 and/or backsheet 18. In some embodiments, however, further differentiation may be necessary to provide the desired extensibility and coefficient of friction properties. For example, intermediate belt segment 38 may be apertured such as by a laser (e.g., decreasing return forces in the intermediate belt segment) and/or an elastic strand, film, laminate, etc. may be added to the upper and lower belt segments 32, 36 (e.g., increasing return forces in the upper and lower belt segments). Activation in the longitudinal as well as the lateral directions may be desired in some embodiments to provide both longitudinal and lateral extensibility.

In some embodiments, the upper belt segment 32, intermediate belt segment 38 and/or lower belt segment 36 may be formed by separate strips of material bonded together, e.g., using elastic glue with the lower belt segment bonded to the topsheet 16 and/or backsheet 18, as an example. For example, in an embodiment, the upper belt segment 32 and/or lower belt segment 36 may be formed of strips of an elastomeric material such as natural or synthetic rubber or synthetic polyurethane such as LYCRA. The intermediate belt segment 38 may be formed of an elastomeric sheet or laminate, for example, that is cut or apertured or otherwise altered to achieve the above described extensibility. Additionally, the intermediate belt segment 38 may be coated with a material to provide a low coefficient of friction, such as lotions, oils and the like. While elastic glue is an example of a material that may be used to bond segments together, any suitable bonding material and/or process may be used that does not substantially alter the desired elastic properties of the upper, intermediate and lower belt segments 32, 36, 38 described above.

Various methods for forming structures having increased coefficient of friction are disclosed in U.S. Pat. No. 5,858,013 issued Kling on Jan. 12, 1999; U.S. Pat. No. 6,626,879 issued to Ashton et al. on Sep. 30, 2003; U.S. Pat. No. 6,641,568 issued to Ashton et al. on Nov. 4, 2003; U.S. Pat. No. 6,918,900 issued to Johnson on Jul. 19, 2005; U.S. Pat. No. 6,746,434 issued to Johnson et al. on Jun. 8, 2004; U.S. Pat. No. 6,478,784 issued to Johnson et al. on Nov. 12, 2002; U.S. Pat. No. 5,782,819 issued to Tanzer et al. on Jul. 21, 1998; U.S. Pat. No. 6,746,433 issued to Shimoe et al. on Jun. 8, 2004; U.S. Pat. No. 6,258,076 issued to Glaug et al. on Jul. 10, 2001; EP 0 873 739 entitled "Absorbent Article Comprising Dual Fixation Means Comprising Topical Adhesive Attachment."

Materials having directional dependent coefficients of friction may also be used to form the upper belt segment 32 and the lower belt segment 38. For example, the upper and/or lower belt structures 32 and 36 can be formed of a material selected to provide a higher coefficient of friction to inhibit movement of the diaper 10 in the downward direction (i.e., toward the feet when standing) and a lower coefficient of friction to facilitate movement of the diaper in the upward direction (i.e., toward the head when standing). Such directional dependent coefficients of friction can be particularly beneficial in pant embodiments when applying and removing the pant. Exemplary directional dependent materials and selective placement of high friction materials are described in U.S. Pat. Nos. 6,626,879 and 5,782,819 referred to above.

In the embodiment of FIG. 1, front closure zones 90 in which the barrier leg cuffs 24 are bonded to the topsheet 16 terminate at the lower belt segment 36 at the front waist region 50. In some embodiments, the back closure zones 92 in which the barrier leg cuffs 24 are bonded to the topsheet 16 terminate at the lower belt segment 38 at the back waist region 52. In an alternative embodiment, both of the front closure zone 90 and the back closure zone 92 may terminate inboard of the lower belt segment 36 of the corresponding front and back waist regions 50, 52. By locating the tackdown point of the barrier leg cuff 24 at the lower belt segment 36, the anchoring point of the force applied by the barrier leg cuff is low on the belt and near the hips which may result in decreased sagging. Additionally, the upper belt segment 32 is spaced apart and decoupled from the lower belt segment 36 using the intermediate belt segment 38, which may further reduce the likelihood of sagging.

The absorbent core 20 may be any absorbent means which is generally compressible, conformable, non-irritating to the wearer's skin, and capable of absorbing and retaining liquids such as urine and other certain body exudates. As shown in FIG. 1, the absorbent core 20 has a garment surface 130, a body surface 132, side edges 134, and waist edges 136. In the illustrated embodiment, the waist edges terminate inboard of the lower belt segment 36 in each of the first and back waist regions 50, 52. In other embodiments, the absorbent core 20 may extend into the belt structure 30 in one or both of the waist regions 50, 52, which can provide a longer absorbent core. In some embodiments where the absorbent core 20 extends into the belt structure 30, the absorbent core is unattached directly thereto, freely residing within the belt structure, e.g., so as not to interfere at least substantially with the elastic and frictional properties described above.

The absorbent core 20 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue and nonwoven wraps and tissue as well as nonwoven laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 20 should, however, be compatible with the design leading and the intended use of the diaper 10. Further, the size and absorbent capacity of the absorbent core 20 may be varied to accommodate wearers ranging from infants through adults.

Exemplary absorbent structures for use as the absorbent core assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997; and U.S. Patent application number 2004/0162536 published on Aug. 19, 2004 entitled "Comfortable Diaper."

The backsheet 18 is positioned adjacent the garment surface 130 of the absorbent core 20 and is preferably joined thereto by attachment means (not shown) such as those well known in the art. For example, the backsheet 18 may be secured to the absorbent core 20 by a uniform continuous layer of adhesive, a patterned layer of adhesive, or an array of separate lines, spirals, or spots of adhesive. In some instances, the topsheet 16 and/or backsheet 18 are attached to the absorbent core 20 after the belt structure is formed. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment may include an open pattern network of filaments of adhesive as is disclosed in U.S. Pat. No. 4,573,986 entitled "Disposable Waste-Containment Garment", which issued to Minetola and Tucker on Mar. 4, 1986. An exemplary attachment of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The topsheet 16 is positioned adjacent the body surface 132 of the absorbent core 20 and is preferably joined thereto and to the backsheet 18 by an attachment (not shown) such as those well known in the art. Suitable attachments are described with respect to joining the backsheet 18 to the absorbent core 20. In one embodiment, the topsheet 16 and the backsheet 18 are joined directly to each other in the diaper periphery 60 and are indirectly joined together by directly joining them to the absorbent core 20 by the attachment means (not shown).

Figure 7:
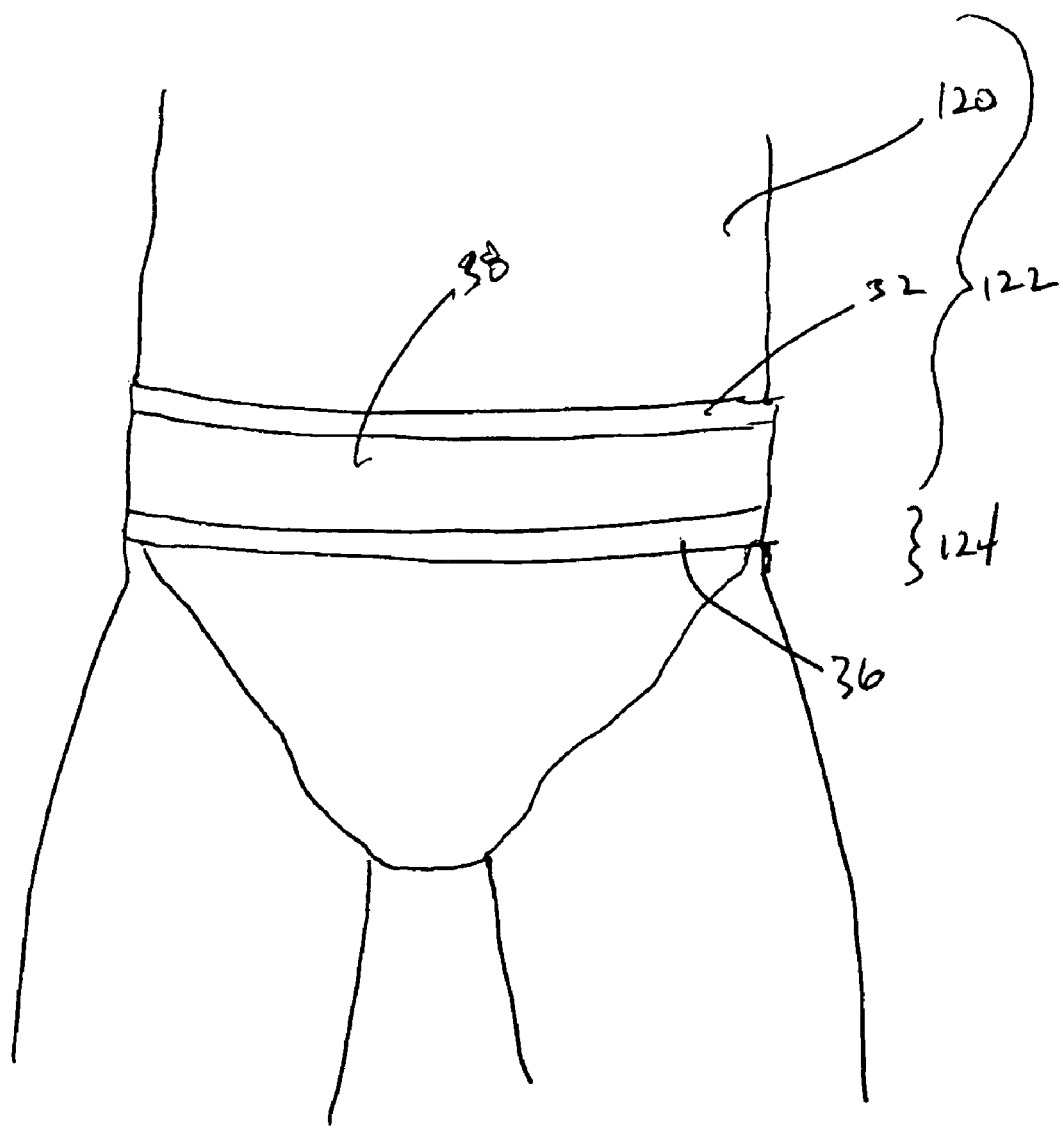
FIG. 7 is a front view of an embodiment of a diaper including multi-segment belt on a wearer.

Referring now to FIG. 7, diaper 10 is applied to the body of a wearer 120. Upper belt segment 32 is located in a higher motion region 122 of the body, lower belt segment 36 is located in a lower motion region 124 of the body and intermediate belt segment 38 is located therebetween. First fastening system 28 (not shown in FIG. 7; see FIG. 1) associated with the upper belt segment 32 serves to provide an upper line of tension used to support the upper belt segment and second fastening system 34 (not shown in FIG. 7; see FIG. 1) serves to provide a lower line of tension longitudinally spaced from the upper line of tension that is used to support the lower belt segment 36 and the core 20. Intermediate belt segment 38 allows the skin of the body to stretch as the body moves.

Referring now to FIGS. 8-12, multi-segment belt structures having the upper, intermediate and lower belt segments 32, 38 and 36 can be used to form absorbent articles that include absorbent assembly 150, for example, that are attached to a separately formed holder 152 (shown by dotted lines). When the absorbent article comprises a separate holder 152 and absorbent assembly 150, the absorbent article includes one or more layers of material forming the holder 152 while the absorbent assembly includes components such as a topsheet 16, a backsheet 18, and an absorbent core 20; see FIG. 8A. While FIGS. 8-12 diagrammatically illustrate only the front waist portions 50 of the multi-segment belt structures, it is to be understood that the absorbent assembly 150 may be attached in a similar or even identical fashion to the back waist portion 52 of the multi-segment belt structures.

Referring to FIG. 8, edge 154 of the absorbent assembly 150 including the absorbent core is joined to a lower edge 156 of the lower belt segment 36 by a bond 165, for example, using an adhesive, such as an elastic adhesive. In this embodiment, the absorbent core 20 is supported entirely below the intermediate and upper belt segments 38, 32.

In the alternative embodiment of FIG. 9, the absorbent assembly 150 is joined to the lower belt segment 36 using attachment members 158 in the form of strips that extend in both longitudinal and lateral directions. The attachment members 158 locate pulling forces nearer a wearer's hips, for example, as opposed to the wearer's front and back, which can reduce the likelihood of sagging. The attachment members 158 also provide a lateral pulling component that may increase tension in the lower belt segment 36. In some embodiments, the absorbent assembly 150 including absorbent core 20 extends into the belt structure 160 (illustrated by dotted lines). Optionally, the absorbent assembly 150 may include a stiffening component, such as a bond 162 to aid the absorbent assembly in maintaining a vertical, standing orientation.

In some embodiments, it may be desirable to affect the extensible properties of one or more of the belt segments 32, 36, 38, for example, at preselected regions. As one example, in embodiments where the absorbent article, such as a diaper, pant and the like utilizing a multi-segmented belt structure as described above, slides into position on the wearer, it may be desirable to make one or more regions of the intermediate belt segment less extensible in the longitudinal direction than an adjacent region of the intermediate belt segment due to the highly extensible, low return properties of the intermediate belt segment 38. These less extensible regions may correspond to grasping locations where the wearer can apply a pulling force without greatly stretching the intermediate belt segment 38, which can facilitate proper placement of the upper belt segment 32 on the wearer's body. This may be desirable for pant constructions. In some embodiments, the less extensible regions may affect the extensibility of a belt segment 32, 38, 36 without corresponding to a grasping location.

Referring to FIG. 10, a longitudinally extending stiffening member such as bond 164 is used to maintain the absorbent assembly 150 in an upright, standing position within the belt structure 30. While a single, somewhat linear bond 164 is shown, any suitable bond pattern can be utilized to desirably reduce the extensibility of one or more of the belt segments 32, 38, 36, such as bond patterns including multiple lines, dots, zigzags, crisscrossing lines, or any combination thereof. Liner 150 including the absorbent core 20 may be also joined to lower edge 156 using bond 165.

Referring to FIG. 11, absorbent assembly 150 is provided with an extensible structure 172 that allows for expansion of the longitudinal length of the absorbent assembly, for example, with little or no additional return forces being applied to the upper belt segment 32. Absorbent assembly 150 is bonded to lower edge 156 of the lower belt segment 36 by bond 165 and to lower edge 166 of the upper belt segment 32. In some embodiments, by joining the less laterally extensible absorbent assembly 150 to the lower belt segment 36 with bond 165, the lateral extensibility of parts of the lower belt segment 36 can be inhibited.

FIG. 11A shows a section view of the extensible structure 172 in a relatively relaxed state. Extensible structure 172 is an accordion-type structure that includes multiple, extensible undulations 168 that allow the longitudinal length of the absorbent assembly 150 to be extended. The number and size of the undulations 168 can be selected to provide a desired amount of longitudinal expansion for the absorbent assembly 150.

Figure 12:
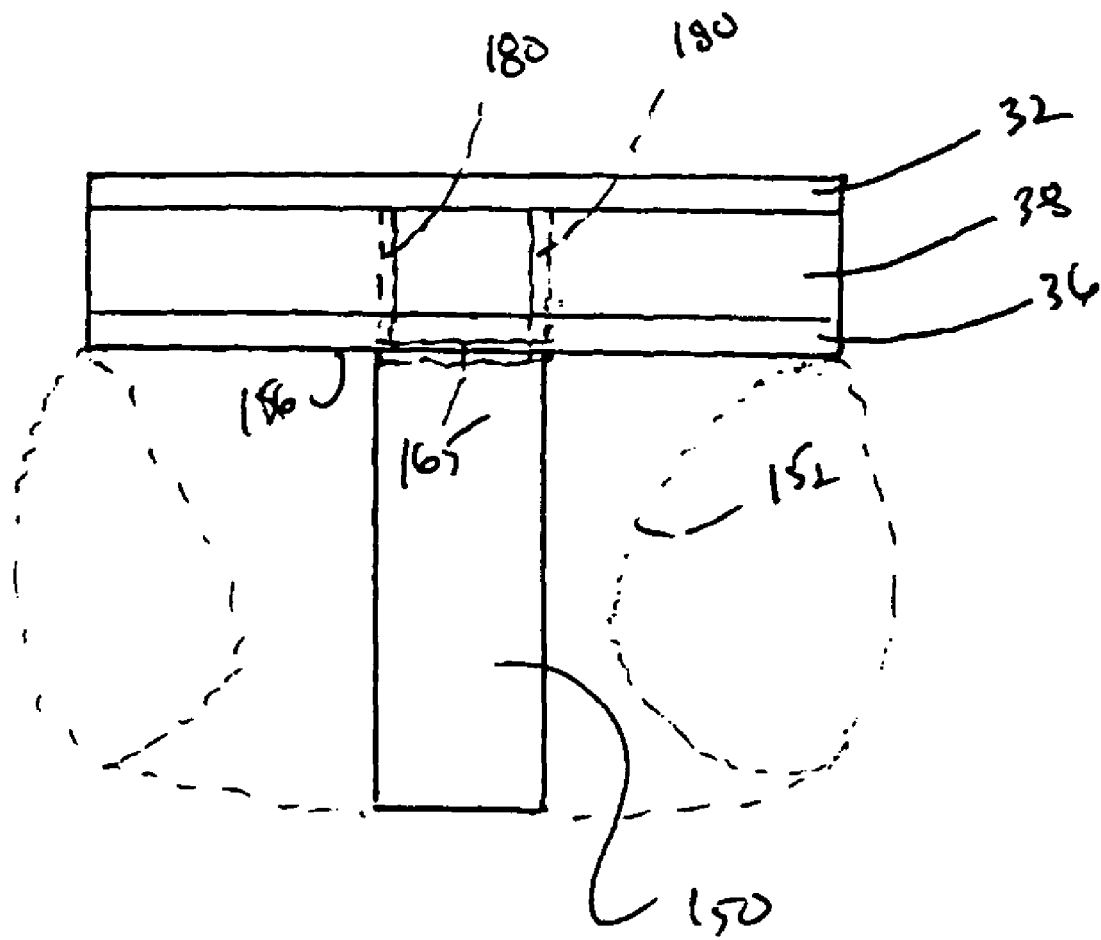
FIG. 12 is a front view of another embodiment of an absorbent article.

A core stiffener 180 is shown in FIG. 12 that is used to stiffen the portion of the absorbent assembly 150 located in the belt structure 30. This may provide added structural support for the absorbent assembly 150. In this embodiment, the absorbent assembly 150 may only be joined to the belt structure 30 at the lower edge 156 of the lower belt segment 36 by bond 165.

Figure 13:
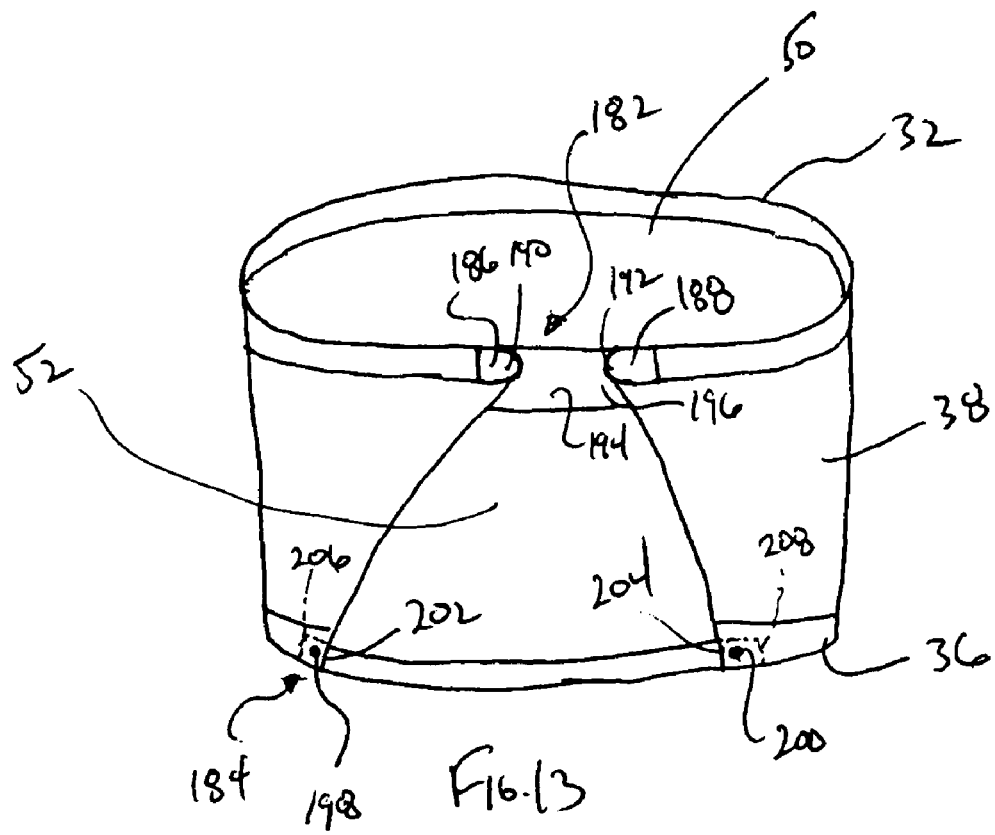
FIG. 13 is a back view of an embodiment of a multi-segment belt structure.

FIGS. 13-20 illustrate various fastening systems that can provide desirable tension properties in the associated belt structures including the upper, intermediate and lower belt segments 32, 38 and 36. Referring first to FIG. 13, the belt structure includes a first fastening system 182 associated with upper belt segment 32 and a second fastening system 184 associated with the lower belt segment 36. First fastening system 182 includes a first fastening member 186 and a second fastening member 188 attached at opposing sides 190, 192 of the upper belt segment 32 at the front waist region 50 and a third fastening member 194 forming a landing zone 196 that is capable of mating with both of the first and second fastening member. In the illustrated example, second fastening system 184 is a passive fastening system that engages once the first fastening system engages without any additional action. Second fastening system 184 includes a first fastening member 198 and a second fastening member 200 attached at opposing sides 202, 204 of the lower belt segment 36 at the front waist region 50 and a third fastening member 206 and fourth fastening member 208 joined to the lower belt segment 36 at the back waist region 52 capable of engaging the first and second fastening members 198, 200.

Figure 14:
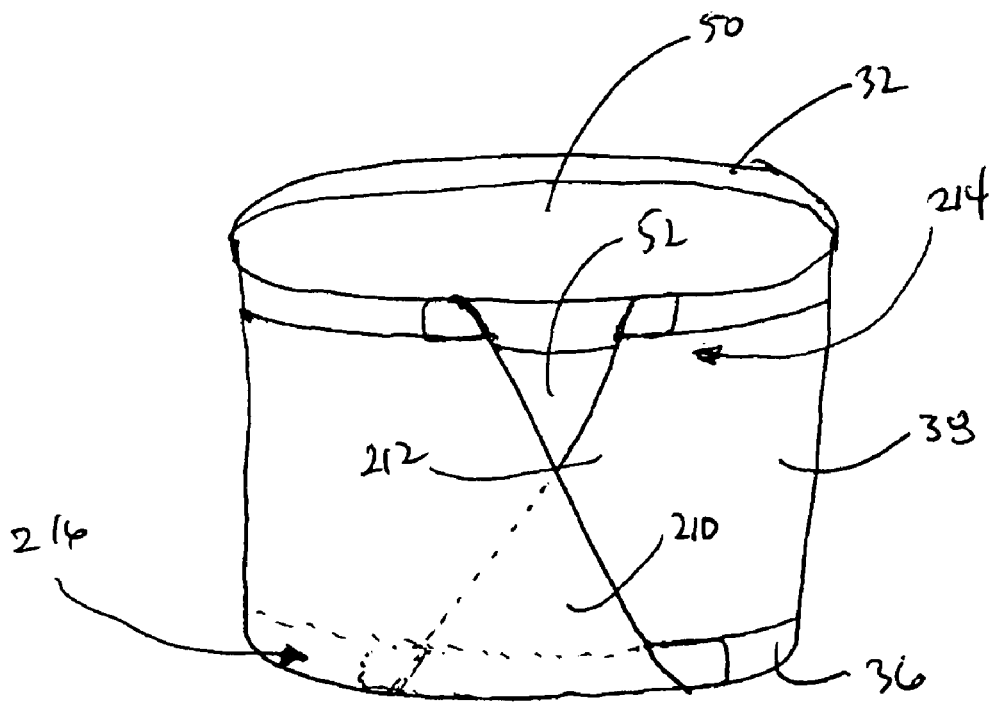
FIG. 14 is a back view of an embodiment of a multi-segment belt structure.

FIG. 14 shows an embodiment including a front waist region 50 having overlapping ears 210 and 212 during use. First fastening system 214 associated with the upper belt segment 32 is a passive fastening system that engages once the second fastening system 216 associated with the lower belt segment 36 engages without any additional action.

Figure 15:
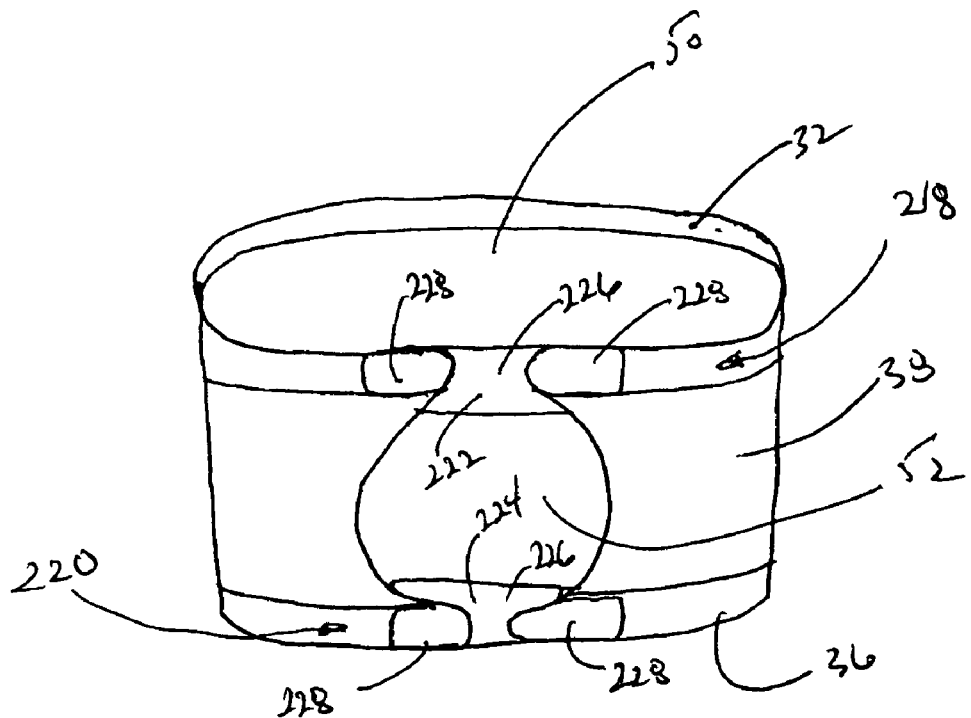
FIG. 15 is a back view of another embodiment of a multi-segment belt structure.

In some embodiments, such as that exemplified by FIG. 15, each first and second fastening system 218, 220 may be active (i.e., non-passive). In this embodiment, the back waist region 52 includes a pair of landing zones 222 and 224 formed by respective fastener components 226, each associated with one of the upper belt segment 32 and the lower belt segment 36. The front waist region 50 includes fastener components 228 capable of mating with the fastener components 226 forming the landing zones.

Figure 16:
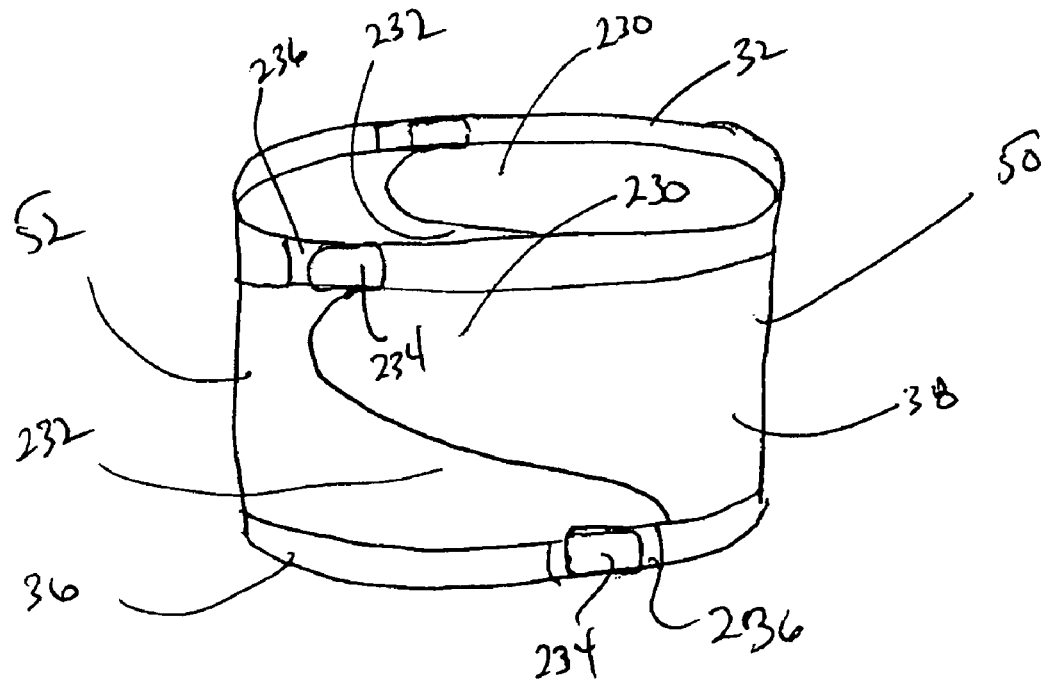
FIG. 16 is a side view of another embodiment of a multi-segment belt structure.

The embodiment of FIG. 16 has front and back waist regions 50 and 52 include ears 230, 232 that overlap each other. In some of these embodiments, each ear 230 and 232 may include differing fastener components for engagement with differing fastener components of the other ear. For example, ear 230 may include a male fastener component 234 (e.g., a hook component) associated with upper belt segment 32 for front-to-back fastening with a female fastener component 236 of ear 232 and a female fastener component 236 (e.g., a loop component) associated with the lower belt segment 36 for back-to-front fastening with a male fastener component 234 of ear 232.

Figure 17:
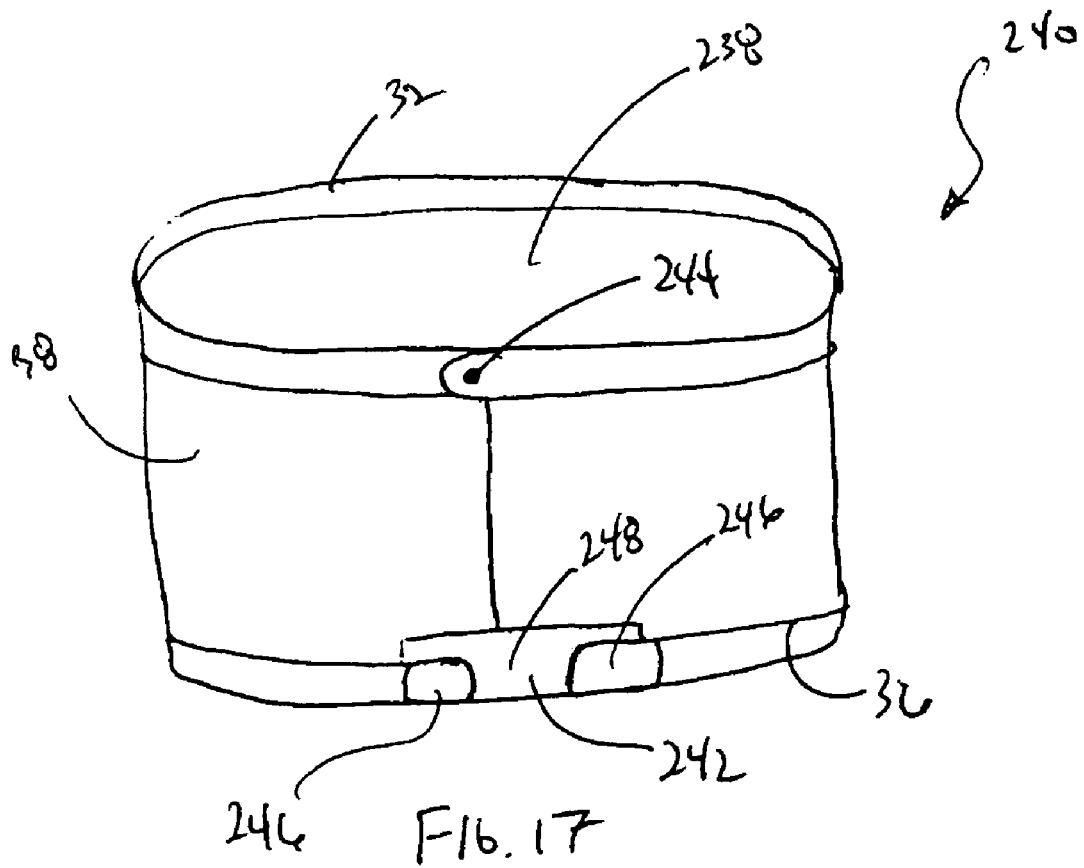
FIG. 17 is a back view of another embodiment of a multi-segment belt structure.
Figure 18:
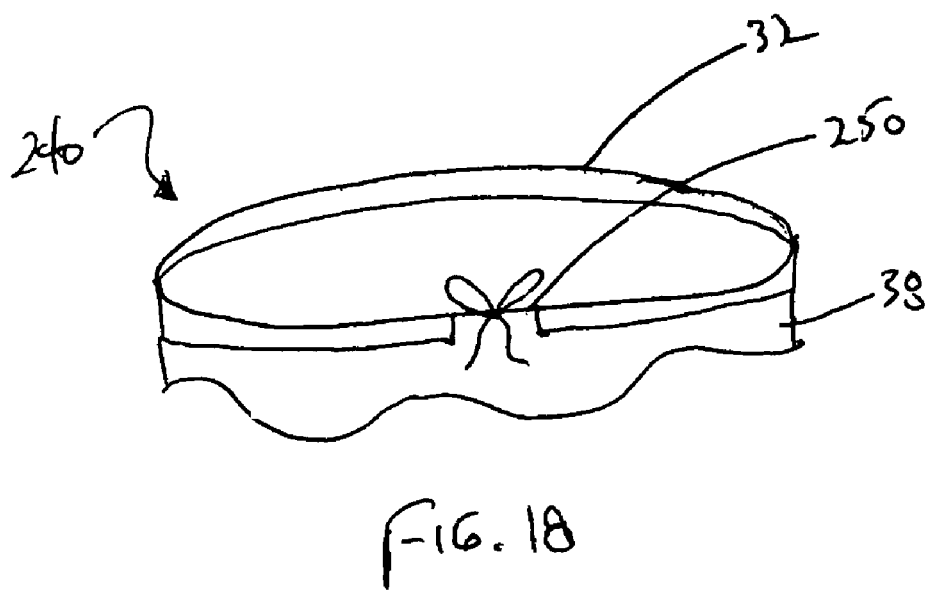
FIG. 18 is a partial view of an alternative embodiment of the multi-segment belt structure of FIG. 17.

While the embodiments of FIGS. 13-16 describe fastening the belt structure to itself using separate front and back waist regions 50, 52 at four fastening locations, there may be other configurations. FIG. 17 illustrates a multi-segment belt structure 240 having a waist region 238 including upper, intermediate and lower belt segments 32, 36 and 38 that can be attached to itself about the body of a wearer. The belt structure 240 can also be affixed (e.g., releasably affixed) to a crotch piece 242, such as a pant or undergarment including absorbent core. Belt structure 240 can be fastened to itself using mating fastening assembly 244 associated with the upper belt segment 32 and can be fastened to the crotch piece 242 using fastening components 246 associated with the lower belt segment 36 and fastening component 248 associated with the crotch piece 242. FIG. 18 illustrates an alternative embodiment that includes a drawstring 250 or other component such as a buckle for use in attaching the belt structure 240 to itself. The drawstring 250 may be attached at an end of the upper belt segment 32 or may reside in pocket (not shown) that extends along an upper edge of the upper belt segment.

Figure 19:
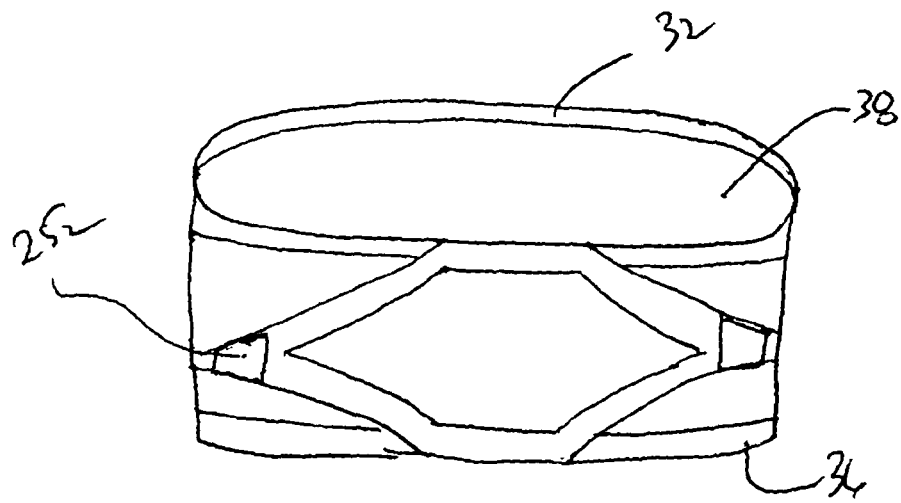
FIG. 19 is a back view of another embodiment of a multi-segment belt structure.
Figure 20:
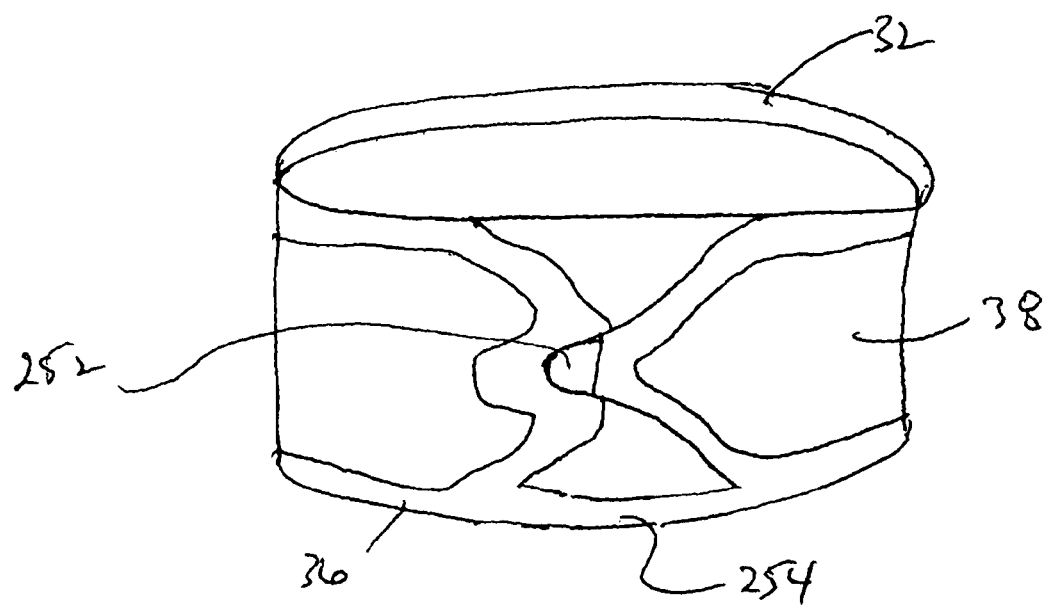
FIG. 20 is a side view of the multi-segment belt structure of FIG. 19.

Referring now to FIGS. 19 and 20, it may be advantageous to reduce the number of fastening components which may be accomplished by locating a fastening location 252 associated with the upper belt segment 32 closer to the lower belt structure 36. The lower location of the fastening component at the lower motion region of the wearer can be chosen to mitigate the fastening system's affect on the extensible properties of the belt structure. A stiffening component 254 may be used to provided added load support.

The above-described fastening systems may employ any suitable mating components such as adhesive fasteners, cohesive fasteners, selective adhesive fasteners, mechanical fasteners, hook and loop fastening components, interlocking fasteners such as tabs & slots, buckles, buttons, snaps, macrofasteners, and/or hermaphroditic fastening components, and combinations of any of these although any other known fastening means are generally acceptable. Some exemplary surface fastening systems are disclosed in U.S. Pat. No. 3,848, 594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in U.S. Pat. No. 6,432,098 entitled "Absorbent Article Fastening Device" in the names of Kline et al. issued on Aug. 13, 2002.

The diaper 10 may also include such other features as are known in the art including graphics, elastics and the like to provide better fit, containment and aesthetic characteristics. Such additional features are well known in the art and are described in U.S. Pat. Nos. 3,860,003; and 5,151,092.

Determining Coefficient of Friction

The static and kinetic coefficient of friction can be measured using ASTM Method D 1894-01 with the following particulars. The test is performed on a constant rate of extension tensile tester with computer interface (a suitable instrument is the MTS Alliance using Testworks 4 Software, as available from MTS Systems Corp., Eden Prarie, Minn.) fitted with a coefficient of friction fixture and sled as described in D 1894-01 (a suitable fixture is the Coefficient of Friction Fixture and Sled available from Instron Corp., Canton, Mass.). The apparatus is configured as depicted in FIG. 1C of ASTM 1894-01 using a stainless steel plane as the target surface. A load cell is selected such that the measured forces are within 10-90% of the range of the cell. The tensile tester is programmed for a crosshead speed of 127 mm/min, and a total travel of 130 mm. Data is collected at a rate of 50 Hz.

The test specimen is cut into a square 6.35 cm by 6.35 cm with its sides parallel and perpendicular to the longitudinal axis of the absorbent article. Any material underneath the functional surface to be tested that would prevent the specimen from being firmly mounted on the sled must be carefully removed. Where the test fabric can only be obtained as a plurality of fabric strips less than 6.35 cm wide, multiple fabric strips are mounted onto the sled. The strips are placed in the same direction as specified above, parallel to one another and as close to each other as possible without overlapping. Whether the specimen is a single piece or a plurality of strips, it is obvious to one skilled with these measurements, that 100% of the surface of the sled must be covered with fabric of the same COF.

The specimen is mounted onto the foam rubber side of the sled using double sided adhesive tape (tape should be wide enough to cover 100% of the sled's surface) with the functional surface facing the stainless steel plane. The specimen is oriented on the sled such that it will be pulled in the direction corresponding to the longitudinal axis of the absorbent article and away from the center transverse axis of the absorbent article. The mass of the sled with mounted sample is recorded to 0.1 gram. The surface of the stainless steel plane is cleaned with isopropanol between each analysis.

The Static and Kinetic COF is calculated as follows:

Static COF=$A_S$/B $A_S$=maximum peak force in grams force (gf) for the initial peak B=mass of sled in grams Kinetic COF=$A_K$/B $A_K$=average peak force in grams force (gf) between 20 mm and 128 mm B=mass of sled in grams While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising:
    a chassis having a front waist region, a back waist region, and a crotch region between the waist regions, laterally opposing closed side edges defining its width, longitudinally opposing front and back waist end edges defining its length, an interior surface and an exterior surface, and including a backsheet;
    an absorbent assembly attached to the chassis; and
    a belt structure disposed in the waist region of the chassis, wherein the belt structure comprises a first belt segment, a second belt segment and a third belt segment, wherein the belt segments are disposed longitudinally with respect to each other and the coefficient of friction of at least a portion of one of the first belt segment and third belt segment is greater than the coefficient of friction of at least a portion of the second belt segment.

2. The disposable diaper of claim 1, wherein the second belt segment is disposed between the first belt segment and the third belt segment.

3. The disposable diaper of claim 1 wherein the second belt segment is longitudinally extensible.

4. The disposable diaper of claim 3 wherein the second belt segment is both longitudinally and laterally elastically extensible.

5. The disposable diaper of claim 1 wherein at least one of the first belt segment and third belt segment is laterally extensible.

6. The disposable diaper of claim 1 wherein the coefficient of friction of at least a portion of the first belt segment is greater than the coefficient of friction of at least a portion of the third belt segment.

7. The disposable diaper of claim 1 wherein the coefficient of friction of at least a portion of the third belt segment is greater than the coefficient of friction of at least a portion of the first belt segment.

8. The disposable diaper of claim 1 wherein the coefficient of friction of at least a portion of the third belt segment is substantially equal to the coefficient of friction of at least a portion of the first belt segment.

9. The disposable diaper of claim 1 wherein the at least one of the first belt segment, second belt segment and third belt segment is laterally discontinuous.

10. The disposable diaper of claim 9 wherein the second belt segment is shorter than at least one of the first belt segment and third belt segment.

11. The disposable diaper of claim 1 wherein at least one of the first belt segment and third belt segment comprise laterally spaced regions of greater coefficient of friction disposed adjacent regions of lesser coefficient of friction.

12. The disposable diaper of claim 1 wherein the interior surface of at least one of the first belt segment and third belt segment has a greater coefficient of friction than the exterior surface of the same belt segment.

13. The disposable diaper of claim 1 wherein the first belt segment in the front waist region and the first belt segment in the back waist region are disposed at the waist end edge.

14. The disposable diaper of claim 1 wherein the distance of the first belt segment from the lateral centerline in at least one of the front waist region and back waist region is less than the distance of the first belt segment from the lateral centerline in the opposing waist region.

15. The disposable diaper of claim 1 wherein the longitudinal spacing between the first belt segment and the third belt segment in at least one of the front waist region and back waist region is greater than the longitudinal spacing between the first belt segment and the third belt segment in the opposing waist region.

16. The disposable diaper of claim 1 wherein the longitudinal spacing between the first belt segment and the third belt segment at the longitudinal centerline in the front waist region is greater than the longitudinal spacing between the first belt segment and the third belt segment at the longitudinal centerline in the opposing waist region.

17. The disposable diaper of claim 1 wherein the longitudinal spacing between the first belt segment and the third belt segment at the longitudinal centerline in the front waist region is greater than the longitudinal spacing between the first belt segment and the third belt segment at the longitudinal centerline in the opposing waist region and wherein at least one of the first belt segment and the third belt segment comprises an arcuate shape.

18. The disposable diaper of claim 1 comprising a crotch point wherein the distance between the crotch point and at the first belt segment in a first waist region is greater than the distance between the crotch point and the first belt segment in the opposing waist region.

19. The disposable diaper of claim 1 wherein the third belt segment has a lateral length that is less than a lateral length of the first belt segment.

20. The disposable diaper of claim 1 wherein the belt structure is disposed in both the front waist region and the back waist region.

21. The disposable diaper of claim 20 further comprising a fastening system for use in fastening the belt structure disposed in the front waist region to the belt structure disposed in the back waist region to form a first tension band and a second tension band longitudinally spaced from the first tension band.

22. The disposable diaper of claim 21 wherein the first and second tension bands are separated by one of the belt segments.

23. The disposable diaper of claim 1 wherein at least one of the belt segments is a continuous loop that is sized and configured to be positioned about the waist of a wearer.

24. The disposable diaper of claim 1 wherein at least one of the belt segments has a portion having a directional dependent coefficient of friction.

25. The disposable diaper of claim 1 wherein the portion of one of the first belt segment and third belt segment having the greater coefficient of friction than the coefficient of friction of at least the portion of the second belt segment is liquid permeable.

26. The disposable diaper of claim 1 wherein the static coefficient of friction of the portion of one of the first belt segment and third belt segment is greater than the static coefficient of friction of at least the portion of the second belt segment.

27. The disposable diaper of claim 1 wherein the kinetic coefficient of friction of the portion of one of the first belt segment and third belt segment is greater than the kinetic coefficient of friction of at least the portion of the second belt segment.

28. A method of forming a disposable diaper, the method comprising:
attaching an absorbent assembly to a chassis, the chassis having a front waist region, a back waist region, and a crotch region between the waist regions, laterally opposing closed side edges defining its width, longitudinally opposing front and back waist end edges defining its length, an interior surface and an exterior surface, and including a backsheet and a topsheet; and
forming a belt structure wherein the belt structure comprises a first belt segment, a second belt segment and a third belt segment, wherein the belt segments are disposed longitudinally with respect to each other and the coefficient of friction of at least a portion of one of the first belt segment and third belt segment is greater than the coefficient of friction of at least a portion of the second belt segment, the belt structure being joined to the chassis.

29. The method of claim 28 wherein the step of forming the belt structure includes mechanically altering at least one of the topsheet and backsheet.

30. The method of claim 29 further comprising forming apertures in at least one of the topsheet and backsheet to form the second belt segment.

31. The method of claim 28 wherein the step of forming the belt structure comprises coating a film with a high friction material to form at least one of the first and third belt segments.

32. The method of claim 28 further comprising forming the chassis, the step of forming the belt structure being performed while forming the chassis.

33. The method of claim 28 wherein the belt structure is formed separately from the chassis and then joined thereto.

* * * * *